July 12, 1966 M. LECOUFLE ETAL Plant Pat. 2,658
ORCHID PLANT
Filed July 30, 1965
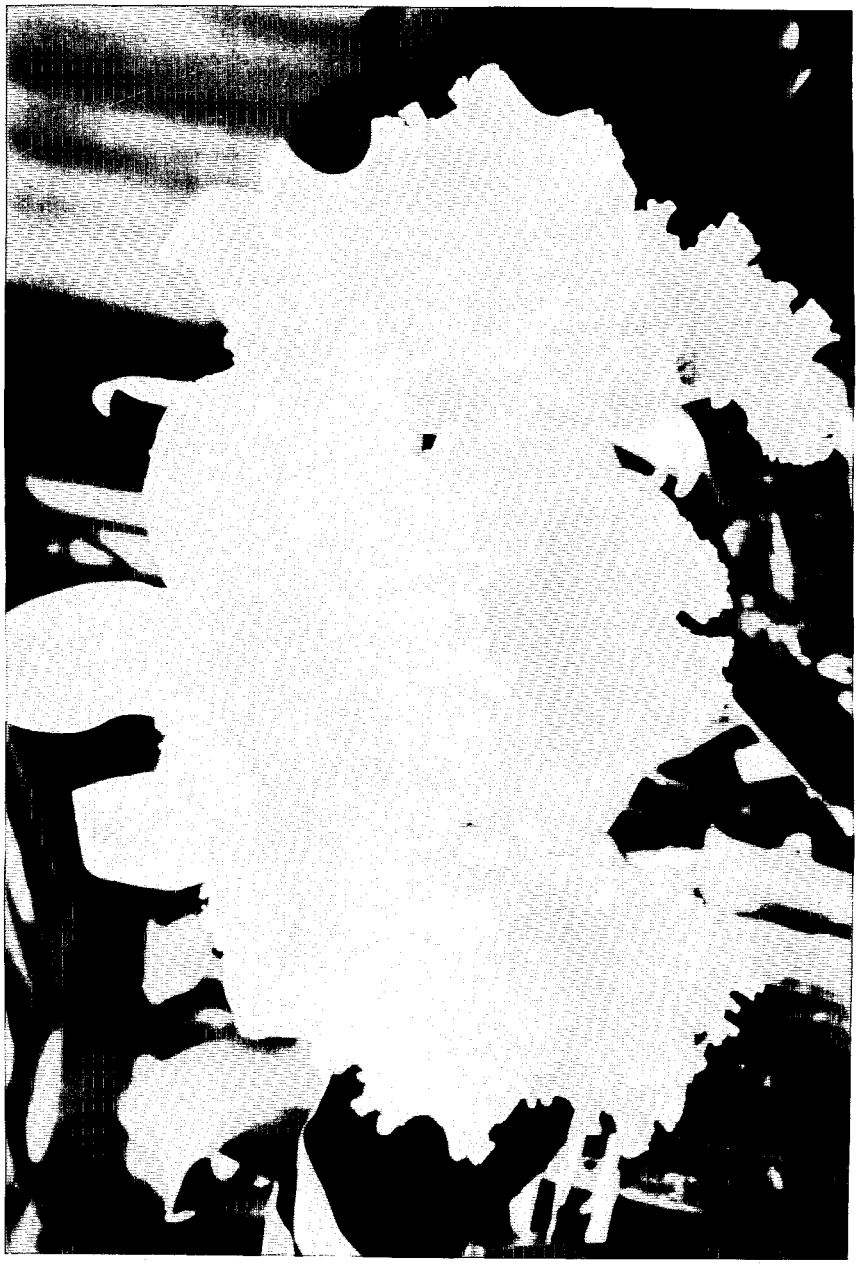
Inventors.
Maurice Lecoufle
Michel Vacherot
By: Robb & Robb
Attorneys.

United States Patent Office

Plant Pat. 2,658
Patented July 12, 1966

2,658
ORCHID PLANT

Maurice Lecoufle and Michel Vacherot, both of Boissy-Saint-Leger, France, assignors to Vacherot & Lecoufle, Boissy-Saint-Leger, France, a partnership Filed July 30, 1965, Ser. No. 476,222
1 Claim. (Cl. Plt.—68)

The present invention relates to a new and distinct variety of Laeliocattleya orchid plant which was originated by us as a selected seedling derived from crossing the Laeliocattleya variety known as "Ile de France" (unpatented) with the Laeliocattleya variety known as "Gaillard" (unpatented), the former being the female parent and the latter being the male parent.

The primary objective of this breeding was to produce a new variety of orchid plant which bears flowers representing an improvement over those of the parent variety "Gaillard," but which possesses the same vigor and flowering ability, while at the same time being fully controllable by photoperiodism. This objective was fully achieved, along with other desirable improvements, as evidenced by the following unique combination of characteristics which are outstanding in our new variety and distinguish it from its parents, as well as from all other varieties of which we are aware:

(1) A strong habit of plant growth;

(2) An ability to break easily to produce side growths;

(3) Abundant flower production, with the flowers usually borne in groups of five flowers well arranged on the spike, and with at least two flowering sprouts growing from the rhizome;

(4) Large flower size and attractive and full shape, with the flower petals being joined and sometimes overlapping;

(5) Excellent texture and substance of the flower petals;

(6) A natural blooming period in the spring around Easter time, while also being fully controllable by photoperiodism; and (7) A distinctive and attractive Orchid Purple general color tonality of the flowers, said color shading lighter and trimming the fringed edges of the flowers, with the flowers having Indian Yellow color beneath the column and gradually fanning out into the veins and becoming yellow patches on the sides.

Asexual reproduction of our new orchid variety, as performed by us in France by meristem tissue culture (a form of botanical division), shows that the foregoing characteristics and distinctions are fixed and come true and are transmissible through succeeding propagations.

The accompanying drawing shows a typical specimen flowering plant of our new variety as depicted in color as nearly true as it is reasonably possible to make the same in a color illustration of this character.

The following is a detailed description of our new orchid variety, as based on observations of specimens grown in France, with color terminology in accordance with Wilson's Horticultural Colour Chart, published in collaboration with the Royal Horticultural Society, except where general color terms of ordinary dictionary significance are obvious:

Breeding: Seedling.
*Female parent.*—Lc. "Ile de France."
*Male parent.*—Lc. "Gaillard."

Propagation: Holds its distinguishing characteristics through succeeding propagations by meristem tissue culture.

*Plant*

Form: Well-branched.

Blooming habit: Usually bears flowers in clusters of 5 flowers per spike.

Blooming season: Spring (around Easter time), but fully controllable by photoperiodism.

Foliage:
*Size.*—Length—from 9 inches to 12 inches. Width—about 3 inches.
*Habit.*—Arched, but otherwise typical of cattleya varieties.
*Texture.*—Smooth.
*Edge.*—Smooth and slightly rounded.
*Color.*—Normal green, but new leaves show some purple spots on upper side while developing.

Bulbs: Protected by several sheaths which are tinted basically Purple on their upper portions, but tending to fade with depth.
*Length.*—From 8½ inches to 10 inches.
*Diameter.*—About 1½ inches.
*Distance between bulbs.*—About 1½ inches.

*Flower*

Borne: Usually in clusters of 5 flowers per spike.

Form: Border of labellum is delicately fringed and closed around the column. Natural spread—about 7¾ inches.

Petals:
*Length.*—About 3¾ inches.
*Width.*—About 3⅜ inches.

Sepals:
*Length.*—About 4 inches.
*Width.*—About 1⅜ inches.

Labellum: Width—about 2½ inches.

Color:
*Labellum.*—Orchid Purple, Plate 31, over lower half of interior, gradually changing to a lighter shade which trims the fringed edge, with Indian Yellow, Plate 6, beneath the column and gradually fanning out into the veins and becoming yellow patches on the sides.
*Petals and sepals.*—From Orchid Purple, Plate 31/1 to Orchid Purple, Plate 32.

We claim:

A new and distinct variety of Laeliocattleya orchid plant, substantially as herein shown and described, characterized particularly as to novelty by the unique combination of a strong habit of plant growth, an ability to break easily to produce side growths, abundant flower production, with the flowers usually borne in groups of five flowers well arranged on the spike, and with at least two flowering sprouts growing from the rhizome, large flower size and attractive and full shape, with the flower petals being joined and sometimes overlapping, excellent texture and substance of the flower petals, a natural blooming period in the spring around Easter time, while also being fully controllable by photoperiodism, and a distinctive and attractive Orchid Purple general color tonality of the flowers, said color shading lighter and trimming the fringed edges of the flowers, with the flowers having Indian Yellow color beneath the column and gradually fanning out into the veins and becoming yellow patches on the sides.

No references cited.

ANTONIO F. GUIDA, *Acting Primary Examiner.*
R. E. BAGWILL, *Assistant Examiner.*